United States Patent [19]

Giordano et al.

[11] Patent Number: 5,606,260
[45] Date of Patent: Feb. 25, 1997

[54] MICRODEVICE FOR MEASURING THE ELECTROMAGNETIC CHARACTERISTICS OF A MEDIUM INCLUDING A SHIELD

[75] Inventors: Patrice Giordano, Pertuis; Henri Glenat, Corenc; Jean-Michel Ittel, La Terrasse; Marcel Locatelli, Montbonnot, all of France

[73] Assignee: Commissariat a l'Energie Atomique, France

[21] Appl. No.: 350,697

[22] Filed: Dec. 7, 1994

[30] Foreign Application Priority Data

Dec. 10, 1993 [FR] France ................................. 93 14871

[51] Int. Cl.⁶ ............. G01V 3/26; G01N 27/72; G01R 33/025
[52] U.S. Cl. ............. 324/339; 324/239; 324/225
[58] Field of Search ............. 324/207.16, 207.17, 324/219, 220, 221, 225, 228, 239, 240, 241, 242, 243, 323, 332, 333, 334, 339, 340, 341, 342

[56] References Cited

U.S. PATENT DOCUMENTS

| | | | |
|---|---|---|---|
| 2,228,293 | 1/1941 | Wurzbach | 324/243 |
| 3,434,046 | 3/1969 | Wilson et al. | 324/221 |
| 3,611,120 | 10/1971 | Forster | 324/241 X |
| 4,030,346 | 6/1977 | Dahle et al. | 73/88.5 R |
| 4,132,980 | 1/1979 | Zabler | 324/207.16 |
| 4,283,681 | 8/1981 | Kazuomi et al. | 324/326 |
| 4,785,247 | 11/1988 | Meador et al. | 324/341 |
| 5,062,307 | 11/1991 | Ikeda et al. | 73/862.36 |
| 5,065,099 | 11/1991 | Sinclair et al. | 324/339 |
| 5,210,492 | 5/1993 | Hosohara et al. | 324/241 X |
| 5,210,495 | 5/1993 | Hapashy et al. | 324/341 |
| 5,361,239 | 11/1994 | Zoeller | 324/338 |

FOREIGN PATENT DOCUMENTS

| | | | |
|---|---|---|---|
| 0177626 | 4/1986 | European Pat. Off. | G01B 7/34 |
| 2288972 | 5/1976 | France . | |
| 471614 | 2/1929 | Germany . | |
| 2431397 | 1/1976 | Germany . | |
| 4013429 | 10/1990 | Germany | G01N 27/83 |

OTHER PUBLICATIONS

H. G. Doll, "Introduction to induction logging and application . . . " Petroleum Transactions, pp. 148–162, 1949.
Wong Cho Chew et al, "Theory of Microinduction Measurements" IEEE Transactions on Geoscience and Remote Sensing, vol. 26, No. 6, Nov. 1988.
D. W. Howard, "Rock susceptibility meter", Journal of Physics E: Scientific Instruments, vol. 9, 1976.

*Primary Examiner*—Sandra L. O'Shea
*Assistant Examiner*—Roger Phillips
*Attorney, Agent, or Firm*—Hayes, Soloway, Hennessey, Grossman & Hage, P.C.

[57] ABSTRACT

A microdevice is provided for measuring the electromagnetic characteristics of a medium in a borehole. The microdevice includes at least one emitting or transmitting coil (31), and at least one receiving coil (41,51). The microdevice generates an A.C. voltage at the terminals of the transmitting coil and measures a signal at the terminals of the receiving coil. The microdevice also includes an E-shaped electrically insulating, soft magnetic material circuit serving as a support for each of the coils and which is positioned adjacent to the medium in the borehole.

33 Claims, 6 Drawing Sheets

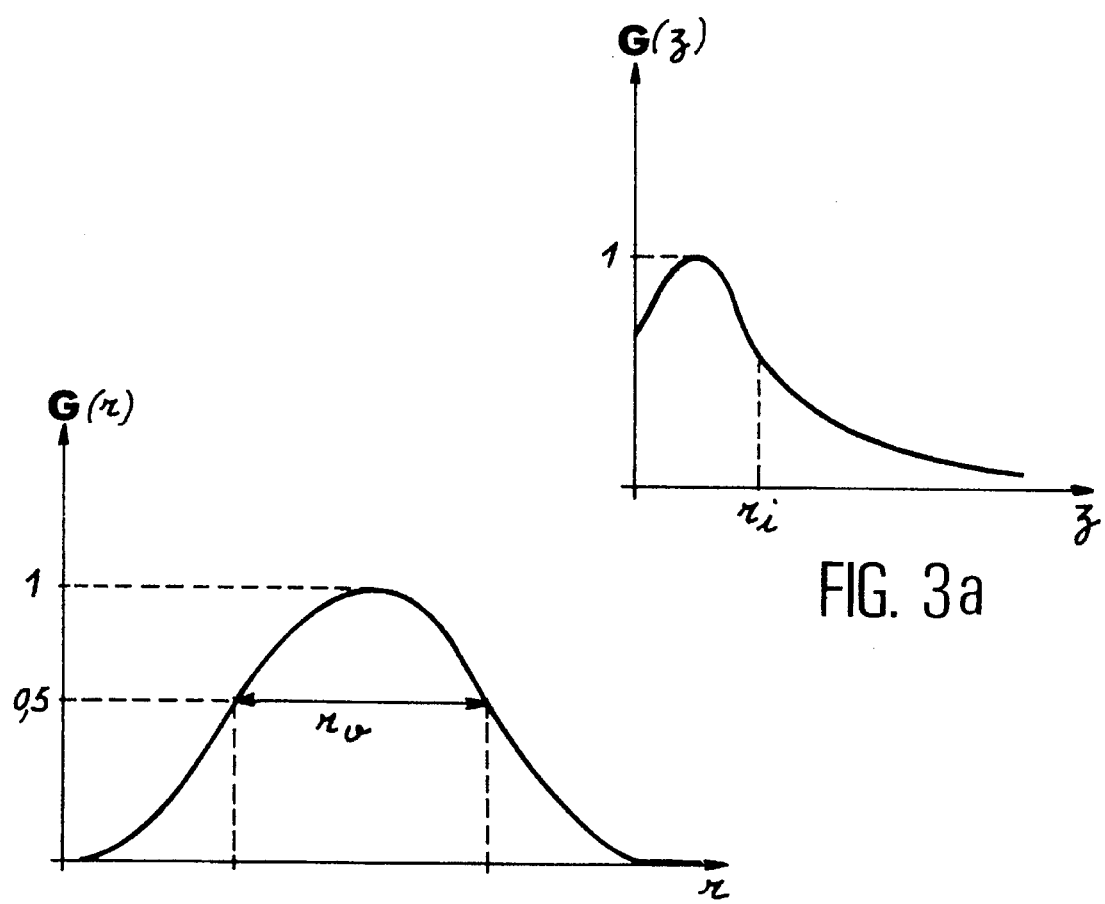
FIG. 3a
FIG. 3b
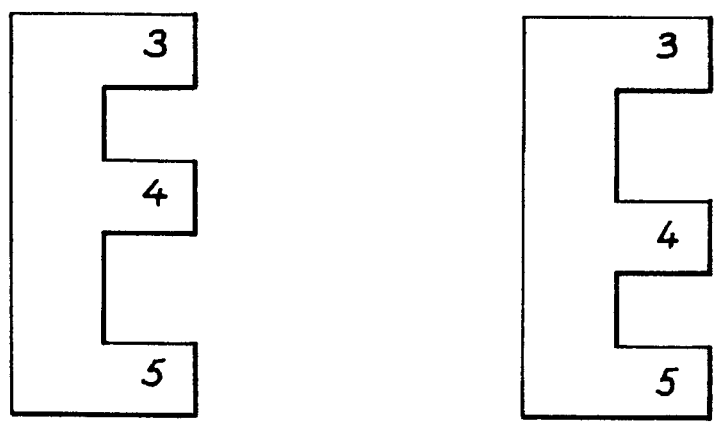
FIG. 4a    FIG. 4b

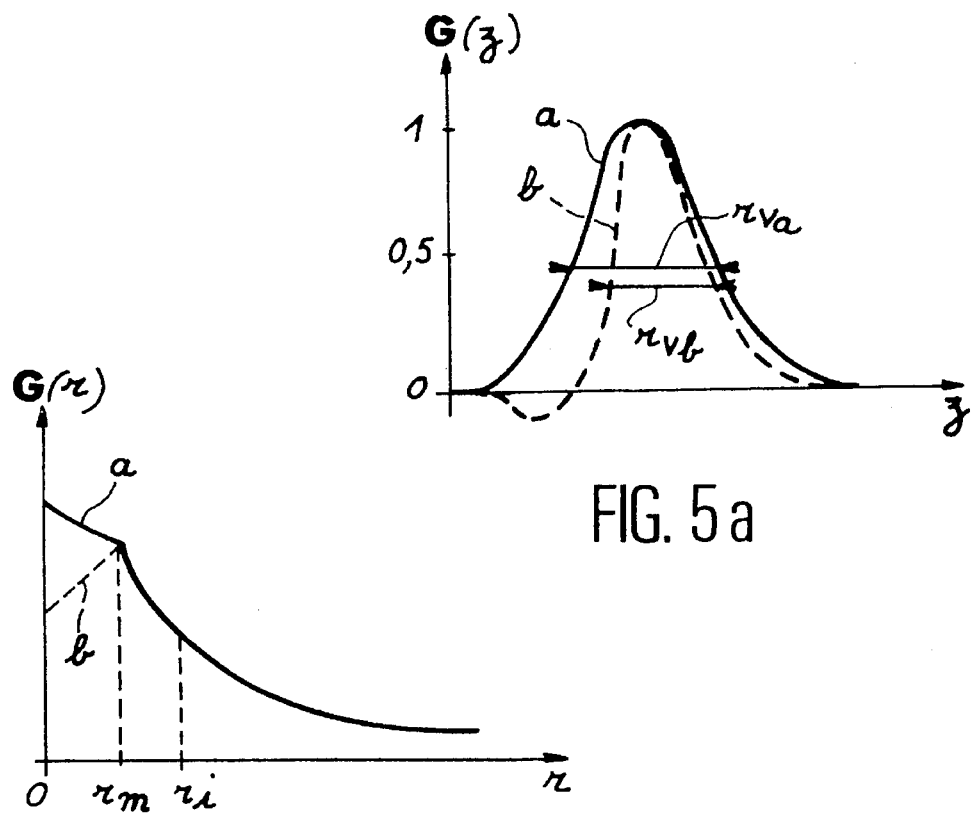
FIG. 5a
FIG. 5b
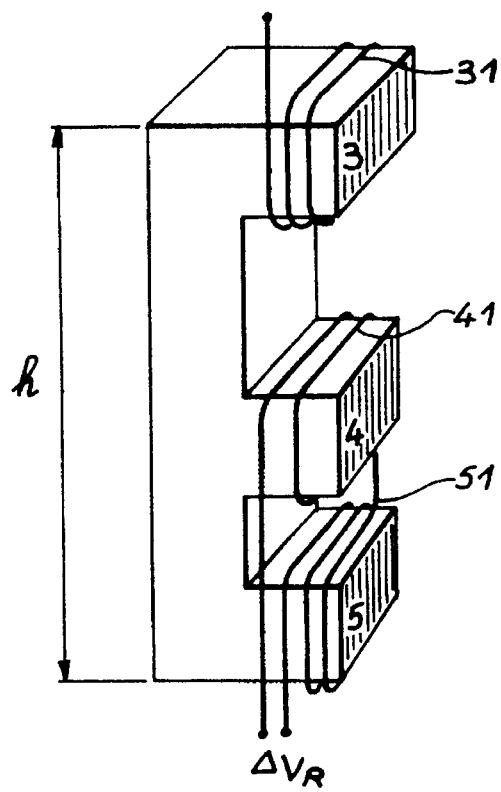
FIG. 6

MICRODEVICE FOR MEASURING THE ELECTROMAGNETIC CHARACTERISTICS OF A MEDIUM INCLUDING A SHIELD

BACKGROUND OF THE INVENTION

1. Field of the Invention

The present invention relates to a microdevice for measuring the electromagnetic characteristics of a medium and the use of said device.

It is used in the field of measuring electromagnetic characteristics of a medium to be checked. An example of such an application is the measurement of characteristics, particularly the conductivity and susceptibility, of geological deposits traversed by a borehole.

2. Brief Description of Related Prior Art

The term "logging" is used to define any continuous measurement of variations, as a function of the depth, of a given characteristic of deposits traversed by a borehole. The first logging tools were introduced by the Schlumberger brothers in 1927. The principle of the measurement consisted of measuring by means of electrodes the electrical resistivity of deposits traversed by boreholes filled with conductive muds. As a result of the ever more frequent use of non-conductive muds, for which the resistivity loggings by electrodes functioned poorly, Doll introduced in 1949 another resistivity logging principle, namely the measurement by electromagnetic induction (H. G. Doll, "Introduction to induction logging and application to logging of wells drilled with oil-based mud", Petroleum Transactions, pp. 148–162, 1949). Numerous devices operating according to one or other of the two aforementioned principles were designed and manufactured, making it possible to determine the resistivities of deposits with a vertical resolution from a few meters to a few dozen centimeters (the vertical resolution of a tool being the measurement of the finest band detectable by the tool).

However, the need to characterize deposits on finer scales for determining their dip has made it necessary to design very small devices, known as microdevices, which are mounted on blocks or pads bearing against the wall of the borehole. These microdevices aim at a good vertical resolution of approximately 1 cm. In the case of electric contact resistivity microdevices, such a resolution can be obtained as a result of the very small size of the electrodes. However, with the increasing use of non-conductive drilling muds, a need has appeared for induction-based conductivity measuring microdevices. The operating principle of such a device, such as is explained in an article by Wong Cho Chew et al entitled "Theory of Microinduction Measurements", (IEEE Transactions on Geoscience and remote Sensing, vol. 26, No. 6, November 1988) is shown in FIG. 1. A low frequency A.C. current $I_E = I_o e^{i\omega t}$ flows in a so-called emitting or transmitting coil 1 producing a magnetic field of the same frequency, which in turn induces eddy currents $I_F$ in the deposit. These eddy currents are proportional to the conductivity of the rock and are phase-shifted by 90° with respect to the emitting or transmitting current. In turn they induce in a so-called receiving coil 2 an electromotive force signal phase-shifted by 180° with respect to the transmitting current. Frequently two receiving coils connected in opposition are used so as to eliminate the direct flux $\phi_1$ generated by the transmitter and so as to only be sensitive to the secondary flux ($\phi_2$) from the deposit. The resultant induced voltage is then directly proportional to the conductivity of the rock.

Despite several theoretical studies, such as that of Chew et al referred to hereinbefore, few practical solutions have been found to the resolution problem defined hereinbefore.

With such induction devices, it is only possible to obtain a vertical resolution of a few centimeters.

In addition, the practical limitations to the use of such devices are numerous, because they are sensitive to the actual drilling fluid, as well as to irregularities in the borehole wall, particularly to stand-off variations (sensor-wall spacing). These two phenomena can lead to interfering signals of greater magnitude than the signal of the deposit. Other interfering signals result from the coupling with other neighboring devices when several of them are located in the same borehole, or from the coupling of the device with the central support of the tool.

SUMMARY OF THE INVENTION

The present invention proposes a simple solution to all these problems.

The present invention therefore relates to a microdevice for logging a medium comprising a transmitting coil and two receiving coils, characterized in that it also comprises an E-shaped, electrically insulating, soft magnetic material circuit adjacent to the medium to be measured and having a median portion and three lateral branches perpendicular to said median portion and parallel to one another, the coils being wound onto said lateral branches in such a way that the receiving coils are located on adjacent lateral branches.

According to a second embodiment of the invention, the magnetic circuit has a median portion and four parallel, lateral branches perpendicular to the median portion.

It can then have two receiving coils located on the two central, lateral branches, between two external lateral branches, each carrying a transmitting coil.

It can also have two transmitting coils located on two central, lateral branches, between two external lateral branches, each carrying a receiving coil.

The central, lateral branches can have different lengths from the outside lateral branches.

According to another embodiment of the invention, the magnetic circuit comprises a median portion and five parallel, lateral branches between which are wound, in this order, a first transmitting coil, a first receiving coil, a second receiving coil connected in opposition to the first receiving coil, a third receiving coil connected in opposition to the second receiving coil and a second transmitting coil.

A microdevice according to the invention, as described hereinbefore makes it possible during the measurement of the electromagnetic characteristics of a geological deposit through a borehole, to achieve a good vertical resolution of approximately 1 cm, a limited coupling with the drilling fluid and with similar, adjacent microdevices and in general a better insensitivity to borehole wall irregularities.

The invention also relates to a method for measuring the electromagnetic characteristics of a medium, using a microdevice as defined hereinbefore. A particular case is that where the characteristics measured are the conductivity and susceptibility of a geological deposit.

With such a method, it is possible to obtain measurements having a good vertical resolution (approximately 1 cm) and only slightly influenced by drilling fluids, any similar, adjacent devices and irregularities of the borehole walls through which the geological deposit is reached.

BRIEF DESCRIPTION OF THE DRAWINGS

The invention is described in greater detail hereinafter relative to non-limiting embodiments and with reference to the attached drawings, in which:

FIGS. 3a and 3b illustrate the vertical and radial characteristics, respectively, for a microdevice according to a first embodiment of the invention.

FIGS. 4a and 4b illustrate two microdevices, respectively, according to a first embodiment of the invention in profile with different separating distances between the two receivers.

FIGS. 5a and 5b illustrate the vertical and radial characteristics, respectively, of microdevices according to FIGS. 4a and 4b.

FIG. 6 illustrates a microdevice according to the invention seen in perspective.

DETAILED DESCRIPTION OF PREFERRED EMBODIMENTS

Figure 2:
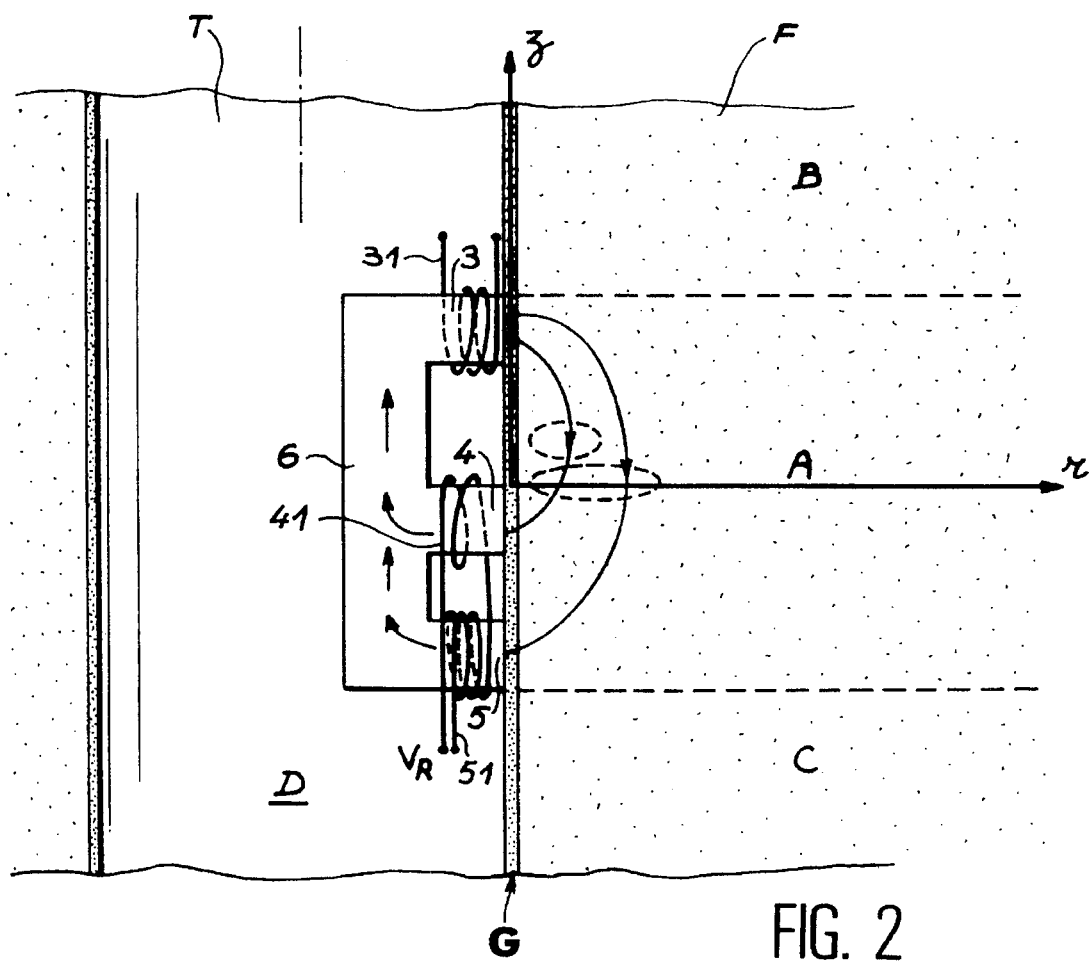
FIG. 2 illustrates a microdevice according to a first embodiment of the invention in position in a borehole.

FIG. 2 illustrates a microdevice for measuring conductivity by induction according to the invention in the measuring position in a borehole. The borehole is in the form of a cylindrical hole T traversing a deposit (F), G representing a mud cake of limited thickness (a few millimeters), against the wall of the deposit F traversed by the borehole.

The device is in the form of an E-shaped magnetic circuit with a median portion 6 and three lateral branches 3,4,5 perpendicular to the median portion and parallel to one another.

In addition, in the embodiment shown in FIG. 2, the lateral portions 3,4,5 are of equal lengths and the two spacings between two adjacent lateral portions 3–4 and 4–5 are different. Onto the lateral branches are wound three windings or coils, namely an emitting or transmitting coil 31 and two receiving coils 41,51, wound in opposition onto two adjacent, lateral branches. The magnetic circuit is preferably constituted by an electrically insulating and magnetically soft material. This material has a relatively high magnetic permeability not varying with the temperature in the useful range (i.e. the range defined between the temperature at the surface of the borehole and the temperature deep in the well and level with the geological deposits traversed, e.g. 0° C. →200° C. Alternatively and in known and predictable manner in such a way that consideration can be given to a correction during or after logging. Thus, this covers materials such as those of the ferrite type, divided iron, iron carbonyl or also materials based on iron in the form of laminated sheets.

The transmitting coil 31 is supplied by a low frequency alternating current $I_0 e^{i\omega t}$ (of a few dozen Hertz to a few dozen kilohertz).

The voltage induced at the terminals of each receiver 41,51 is the sum of two contributions, on the one hand the variation of the direct magnetic flux produced by the transmitter and on the other the variation of the secondary magnetic flux produced by the eddy currents induced in the deposit. So as to only be sensitive to the signal from the deposit, the receivers are wound in opposition and their respective number of turns is correctly adjusted in such a way that the contribution of the direct flux is eliminated. Another way of obtaining such a result is to adjust the cross-section on the ends of the magnetic circuit, because the voltage induced at the terminals of a coil is proportional, not only to its number of turns, but also to its cross-section.

The choice of a "balanced" arrangement has in our case the other advantage of eliminating any disturbance to the signal linked with variations in the magnetic and electrical characteristics of the magnetic circuit during logging.

The use of a soft magnetic circuit adjacent the side of the medium to be measured (E-shaped in FIG. 2) permits the channelling of the magnetic field produced by the transmitting circuit into the deposit of the borehole. Therefore said magnetic field induces eddy currents in the deposit, mainly in an area A (cf. FIG. 2) facing the magnetic circuit and only slightly beyond said area, which by itself eliminates any disturbing signal from "peripheral" areas (areas B,C and D in FIG. 2).

Thus, it is possible to study in a more precise and quantitative manner the coupling of the microdevice with the deposit, e being the measured signal (voltage induced at the terminals of the receiver):

$$e = k \iiint_{rock\ volume} \sigma(x,y,z) S(x,y,z) dxdydz$$

in which:

k is a constant $k = N_R \omega^2$, ($N_R$ being the number of turns and $\omega = 2\pi f$)

$\sigma(x,y,z)$ is the electrical conductivity of the rock at point $(x,y,z)$, $S(x,y,z)$ is the sensitivity at the point $(x,y,z)$, the higher S, the greater the signal from point $(x,y,z)$ of the deposit.

Figure 1:
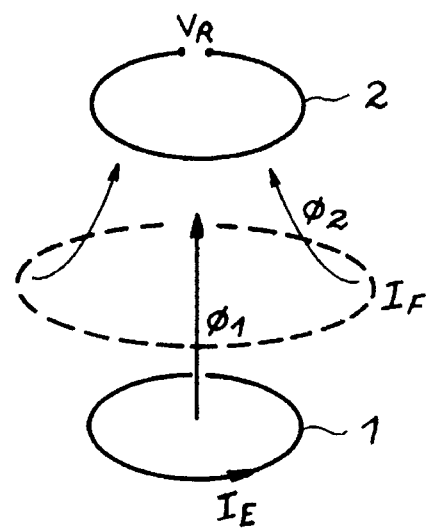
FIG. 1 illustrates the principle of measuring conductivity by induction.

It is possible to use cylindrical coordinates r,θ,z, the axis z being parallel to that of the borehole and chosen in the manner indicated in FIG. 1. Assuming a distribution of the rocks independent of the angle θ, the following radial characteristic is defined:

$$G_r(r) = \int_{-\infty}^{+\infty} S(r,z) dz$$

In this characteristic, it is possible to deduce the "investigation depth", which is the depth $r_i$ for which the area under the curve $G_r(r)$ reaches 50% of the total value of the area (cf. FIG. 3a). Thus, the vertical characteristic $G_v$ is defined:

$$G_v(z) = \int_0^{\infty} S(z,r) dr$$

It is possible to deduce from this curve the "vertical resolution" $r_v$, which is the curve mid-height width (cf. FIG. 3b).

FIGS. 4a and 4b show two microdevices according to the invention. The difference between them is the distance between the two parts 4,5 of the circuit on which the receivers 41,51 are wound. This distance is greater in the microdevice of FIG. 4a than in that of FIG. 4b. On the basis of the corresponding radial and vertical characteristics shown in FIGS. 5a and 5b, it is clear that a vertical resolution of 14 to 18 mm (FIG. 5a) and an investigation depth (FIG. 5b) of approximately 13 mm (13.7 mm, the same in both cases) are obtained. However, in the best possible cases, the existing microdevices have an investigation depth of 1 cm for a vertical resolution of 3 to 5 cm in insulating mud. Thus, as a result of the configuration according to the invention, there is an improvement to the vertical resolution by approximately a factor of 2, there being no deterioration to the investigation depth.

On the basis of FIGS. 5a and 5b, it can be seen that the closer the receiver 41 is to the receiver 51, the finer the vertical resolution, the investigation depth remaining virtually unchanged. It is therefore possible to "adjust" the vertical resolution by choosing a varying distance between the two receivers.

Finally, the closer the receivers are to one another, the less the device is sensitive to interfering signals, which are due on the one hand to the signal from the mud cake G between the measuring device and the borehole wall (cf. FIG. 2) and on the other hand to the variations in the sensor-wall distance. Thus, in the device of FIG. 4b, the radial characteristics has a maximum at approximately $r_m$=4 mm (cf. FIG. 5b). This means that the contribution to the signal of the "near" parts (between 0 and 4 mm) of the microdevice is attenuated. It is precisely from these parts that the aforementioned interfering signals come.

Another advantage of the microdevice according to the invention is the weak coupling between several microdevices when they are arranged on several pads or blocks, e.g. for a tiltmetry or clinometry measurement. This avoids having to have recourse to the conventional solutions of multifrequency excitations or switched excitations, which requires much more complex electronics associated with each microdevice. In the same way, the coupling between the central support of the generally metallic tool is greatly reduced.

FIG. 6 shows an embodiment of the invention. Mumétal sheets (Fe-Ni-Mo) with a thickness of 53 μm are arranged so as to form an asymmetrical E-shaped magnetic circuit. In this construction, the transmitting circuit 31 is placed on a lateral branch 3 and the two receivers 41,51 are connected in opposition on the two other branches 4 and 5 in such a way that in the absence of a conductive medium facing the sensor, the resulting voltage is zero. Typically such a device has a height h (cf. FIG. 6) of a few dozen millimeters.

An arrangement in which the transmitting circuit is positioned on the central branch, and wherein the receivers are connected in opposition on the outer lateral branches is more sensitive to wall irregularities than the arrangement in which two receiving coils are wound in opposition on two adjacent lateral branches.

Figure 7:
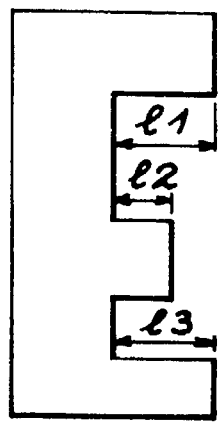
FIG. 7 illustrates another variant of the instant invention with unequal E branches.

FIG. 7 shows another embodiment in which the branches of the magnetic circuit have unequal lengths (e.g. $l_1 \approx l_3 \neq l_2$).

A transmitting circuit is connected on any random one of the extreme lateral branches, each of the other branches supporting a receiving circuit, both connected in opposition.

Figure 8:
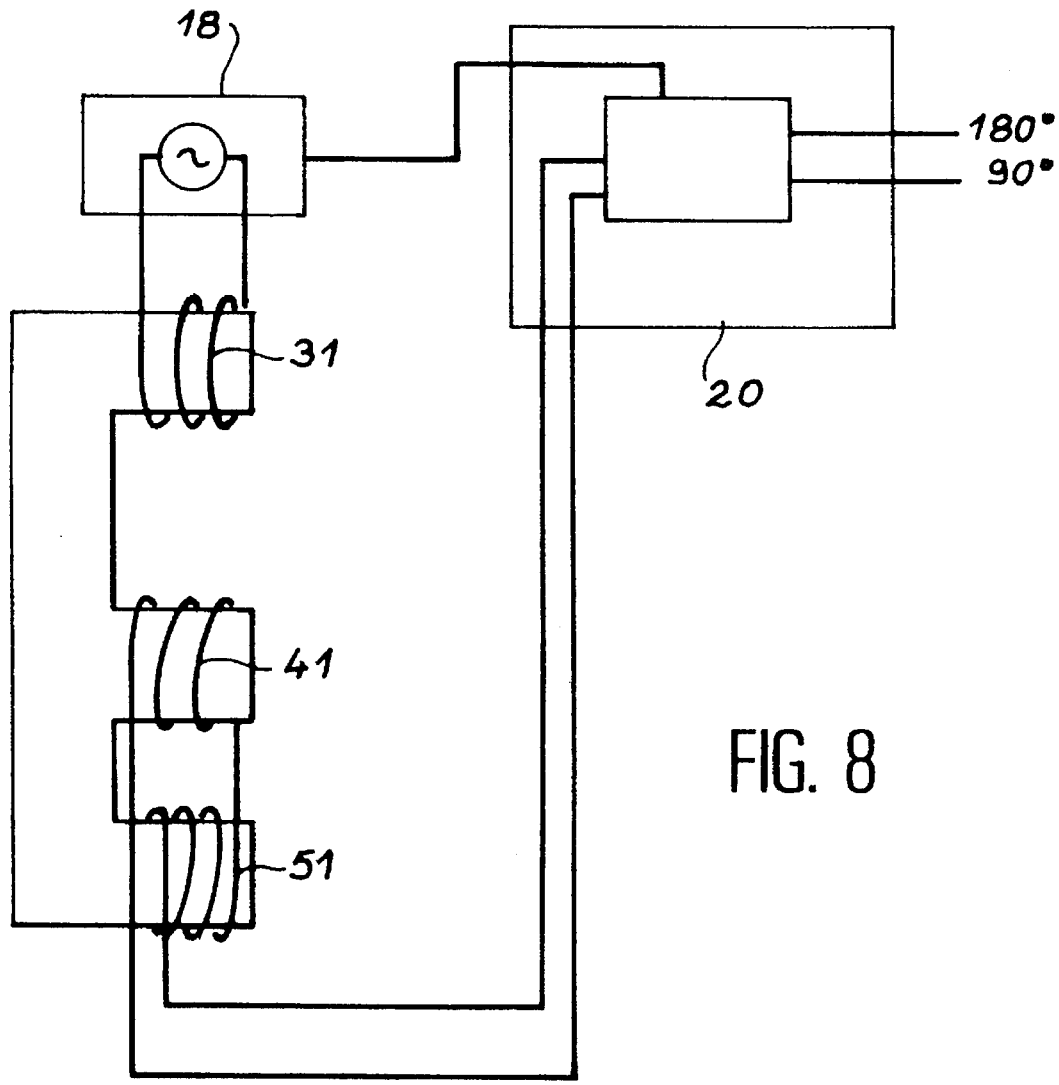
FIG. 8 is a schemation diagram of an electrical arrangement for measuring the signal and characteristics of the median to be investigated, in the case of an E-shaped device.

FIG. 8 illustrates an electronic connection example for a microdevice according to the invention shaped like an E. This microdevice comprises a transmitting coil 31 and two receiving coils 41,51 connecting in opposition. The arrangement incorporates means for generating an A.C. voltage at the terminals of the transmitting coil and means for measuring a signal at the terminals of the receiving coils.

In the case of application to logging by induction in a borehole, the voltage measured in the receiving coils has in fact two components, namely a component at ±180° with respect to the transmitting current which makes it possible to measure the conductivity of the rock and a component at ±90° with respect to the transmitting current and from which it is possible to deduce the susceptibility. Another component at 90° with respect to the transmitting current and corresponding to the direct flux induced by said current in the receiving coils is eliminated by the connection in opposition.

The transmitting coil 31 is supplied by a generator 18, which delivers a phase reference signal to a phase detector 20, to whose input are connected the terminals of receivers (41, 51) connected in opposition.

At the output of the phase detector, two signals, one at 180° and the other at 90° with respect to the reference signal, make it possible to calculate respectively the conductivity and susceptibility of the rock.

Figure 9A:
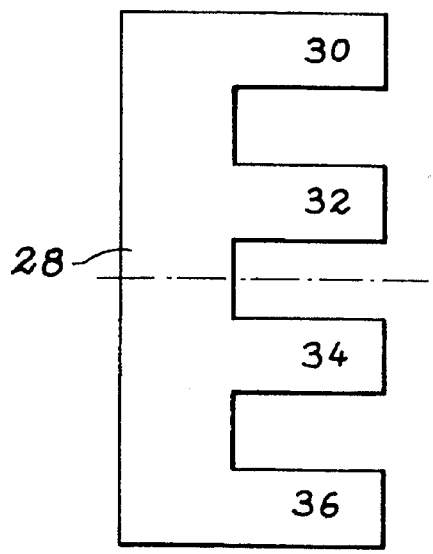
FIGS. 9a, 9b, and 9c illustrate various aspects of a second embodiment of the invention.
Figure 9B:
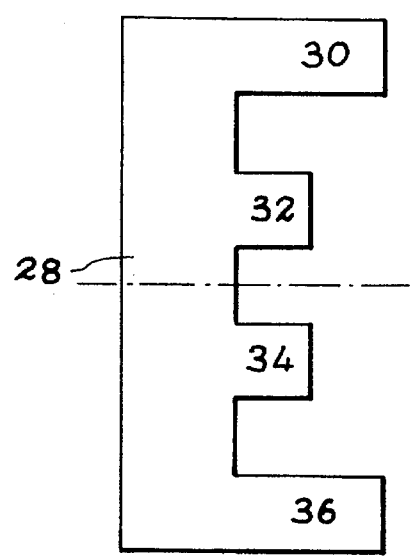
Figure 9C:
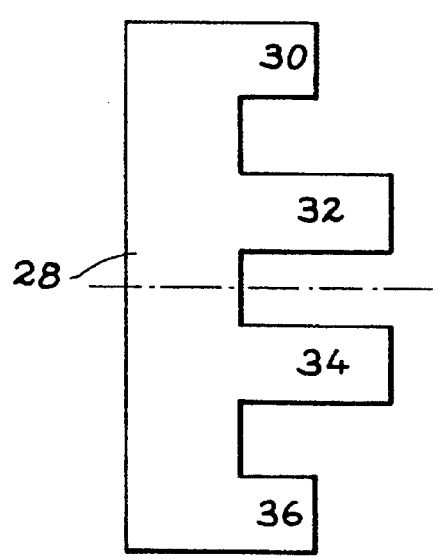

A second embodiment of the invention is illustrated in FIGS. 9a to 9c. In each of the latter an electrically insulating, soft magnetic material circuit has a median portion 28 and four parallel, lateral branches 30,32,34,36 perpendicular to the median portion. Two transmitting coils (not shown) are connected on outer branches 30,36 and are preferably connected in series. Two receiving coils (not shown) are connected on internal branches 32,34 and are preferably connected in opposition.

The measurement of the signal can take place using an electrical circuit with a schematic diagram similar to that of FIG. 8. The transmitting coils are connected to means for generating an A.C. voltage at their terminals and their receiving coils to means for measuring a signal at their terminals.

The two internal branches 32,34 may be are of equal length (FIG. 9a), smaller length (FIG. 9b) or greater length (FIG. 9c) compared to the length of the outer branches 30,36, the compensation of the flux directly induced in the receiving coils by the transmitting coils appearing easier in the first case than in the two latter cases. Naturally, it is possible to reverse the position of the two transmitting coils with those of the two receiving coils.

Figure 10:
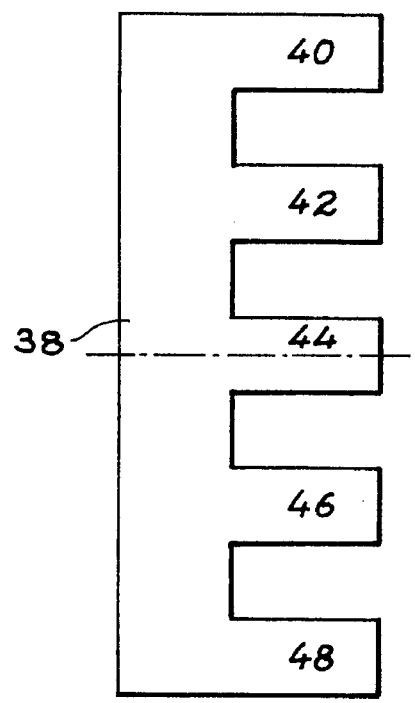
FIG. 10 illustrates a third embodiment of the invention.

A third embodiment of the invention is illustrated in FIG. 10. An electrically insulating, soft magnetic material circuit comprises a median portion 38 and five parallel, lateral branches 40,42,44,46,48 perpendicular to said median portion.

Two transmitting coils (not shown) are connected in series on the outer, lateral branches 40,48 and three, receiving coils are connected on the three outer branches 42,44,46, the centrals receiving coil connected at 44 being connected in series-opposition with the two other receiving coils connected at 42 and 46.

In the two latter embodiments described, it has been possible to realize a very good vertical resolution (approximately 1 cm) and a weak coupling with the fluid of the borehole and with other sensors, if other sensors are used in the same borehole.

Figure 11:
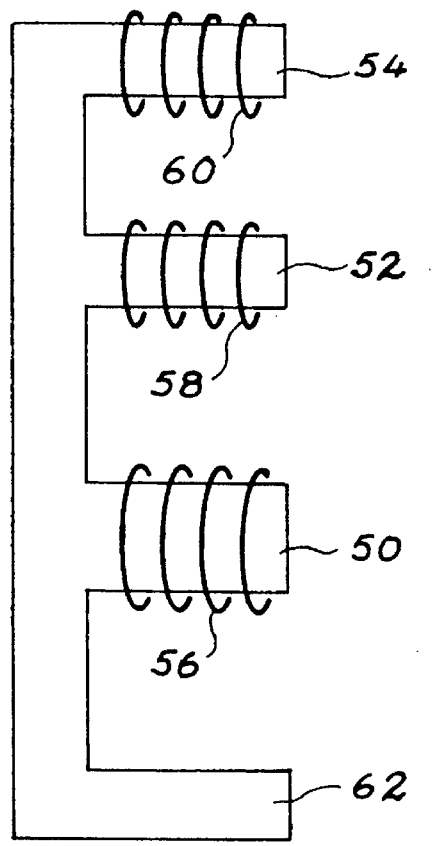
FIGS. 11 and 12 illustrate means for forming a screen between the transmitting coil and part of the environment outside the area of interest.
Figure 12:
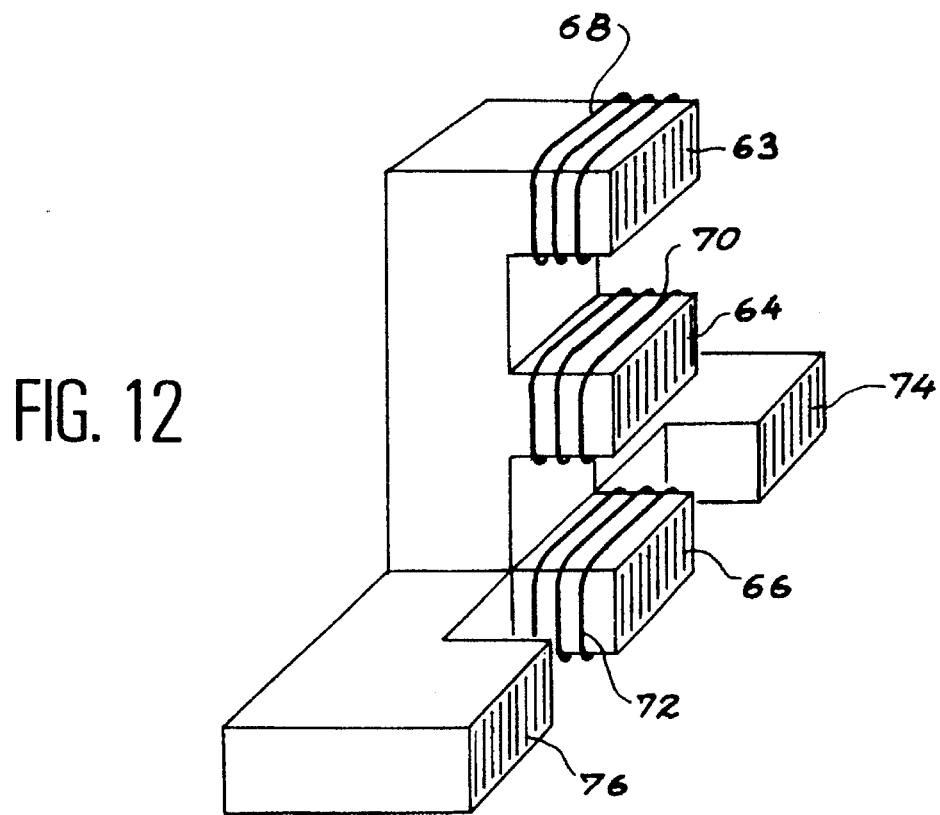

Other embodiments of the invention are illustrated in FIGS. 11 and 12.

To the embodiments of FIGS. 11 and 12 solve the problem of magnetic flux leaks from transmitters to areas of the environment to be measured which lack any interest. For this purpose, adjacent to the branch or branches having a transmitting coil are positioned means for forming a screen or shield between said coil and the area which is of no interest.

Such means can be in the form illustrated in FIG. 11, which diagrammatically shows a device according to the invention having three branches 50,52,54 carrying a transmitting coil 56 (external branch 50) and receiving coils 58,60 (branches 52,54), connected and supplied in the manner described hereinbefore. The device has a supplementary branch 62, e.g. made from the same material as the remainder of the device and on which no coil is wound. This supplementary branch, which is parallel to the other branches and perpendicular to the median portion, is in the vicinity of the branch 50 on which is wound the transmitting coil. Thus, the flux of the latter is not in part lost in the areas of the medium to be measured which are of no interest, so that a better directivity is ensured. Moreover, this embodiment makes it possible to ensure a better decoupling with respect to other sensors. It is possible to adapt a supplementary branch to a device having four or five coils (like those of FIGS. 9a to 10) as soon as a transmitting coil is located on an external branch.

In all cases, it is also possible to adapt on either side of a branch carrying a transmitting coil, with respect to a plane passing through the median portion of the device and through its lateral branches carrying coils. Thus, FIG. 12 shows a device having three lateral branches 63,64,66 on which are wound receiving coils 68,70 and a transmitting coil 72.

On either side of the branch 66 carrying the transmitting coil there are two branches 74,76 not carryng coils and e.g. made from the same material as the rest of the device. These supplementary branches 74,76 have also an effect of channelling the flux to the areas of interest. They also permit a better decoupling with respect to other sensors located in the borehole.

The two solutions described hereinbefore for channelling the flux of a transmitting coil can also be combined.

The invention described is applicable to conductivity and susceptibility logging in geological deposits traversed by boreholes. It can more generally apply to the measurement of the electromagnetic characteristics of electrically conductive materials, e.g. by measuring their conductivity and/or susceptibility.

We claim:

1. A microdevice for logging a medium in a bore hole comprising a transmitting coil and two receiving coils, an E-shaped, electrically insulating, soft magnetic material circuit adjacent the medium and having a median portion and three lateral branches perpendicular to said median portion and parallel to one another, the coils being wound onto said lateral branches in such a way that the receiving coils are located on adjacent lateral branches, said microdevice also comprising means for forming a shield between the transmitting coil and an area lacking interest in the medium.

2. A microdevice according to claim 1, wherein the two spacings between adjacent lateral branches are equal to one another.

3. A microdevice according to claim 1, wherein the two spacings between adjacent lateral branches are different from one another.

4. A microdevice according to claim 1, wherein the lateral branches are of unequal length.

5. A microdevice according to claim 1, and further comprising a supplementary branch on which no coil is wound, said supplementary branch being adjacent the branch on which is wound the transmitting coil.

6. A microdevice according to claim 1, and further comprising two supplementary branches on either side of the branch on which is wound the transmitting coil with respect to a plane passing through the median portion and three lateral branches.

7. A microdevice according to claim 1, wherein the soft magnetic material is selected from the group consisting of ferrite, divided iron, iron carbonyl and a material based on iron in the form of a laminated sheet.

8. A method for measuring electromagnetic characteristics of a medium using a microdevice according to claim 1.

9. A method according to claim 8, wherein the measured characteristics are conductivity and susceptibility of a geological deposit.

10. A microdevice according to claim 1, and further comprising two supplementary branches located on either side of the branch on which is wound the transmitting coil with respect to a plane passing through the median portion an, three lateral branches.

11. A microdevice according to claim 5, and further comprising two supplementary branches located on either side of the branch on which is wound the transmitting coil with respect to a plane passing through the median portion and three lateral branches.

12. A microdevice for logging a medium in a borehole comprising a transmitting coil and two receiving coils, a second transmitting coil, an electrically insulating, soft magnetic material circuit serving as a support for each of the coils and which is adjacent the medium and which has a median portion and four lateral, parallel branches perpendicular to the median portion, said microdevice also comprising means for forming a shield between at least one transmitting coil and an area without interest in the medium.

13. A microdevice according to claim 12, wherein the soft magnetic material is selected from the group consisting of ferrite, divided iron, iron carbonyl and a material based on iron in the form of a laminated sheet.

14. A microdevice according to claim 12, wherein the two receiving coils are located on two lateral, central branches, and two outside lateral branches each carry a transmitting coil.

15. A microdevice according to claim 14, and further comprising a fifth lateral branch parallel to the two lateral central branches and the two outside lateral branches as well as a third receiving coil, the coils being connected in the following order starting from the outermost outside lateral branch: a first transmitting coil, a first receiving coil, a second receiving coil connected in opposition to the first receiving coil, a third receiving coil connected in opposition to the second receiving coil and a second transmitting coil.

16. A microdevice according to claim 12, and further comprising a first supplementary branch on which no coil is wound, and said first supplementary branch being adjacent one of the branches carrying a transmitting coil.

17. A microdevice according to claim 16, and further comprising a second supplementary branch on which no coil is wound and being adjacent the other branch carrying a transmitting coil.

18. A microdevice according to claim 12, and further comprising two supplementary branches located on either side of one of the branches carrying a transmitting coil, with respect to a plane passing through the median portion and lateral branches carrying coils.

19. A microdevice according to claim 12, wherein the two transmitting coils are located on the two central, lateral branches, and the two outside lateral branches each carrying a receiving coil.

20. A microdevice according to claim 19, and further comprising two supplementary branches located on either side of at least one of the branches carrying a transmitting coil, with respect to a plane passing through the median portion and the lateral branches carrying coils.

21. A device comprising a central support for carrying a plurality of microdevices for logging a medium in a borehole, each of said microdevices including a transmitting coil and two receiving coils, an E-shaped, electrically insulating soft magnetic material circuit adjacent the medium and having a median portion and three lateral branches perpendicular to said median portion and parallel to one another, the coils being wound onto said lateral branches in such a way that the receiving coils are located on adjacent lateral branches, each of said microdevices also including means for forming a shield between the transmitting coil and an area lacking interest in the medium.

22. A device according to claim 21 wherein each of said microdevices also includes a supplementary branch on which no coil is wound, said supplementary branch being adjacent the branch on which is wound the transmitting coil.

23. A device according to claim 21, wherein each of said microdevices also includes two supplementary branches on either side of the branch on which is wound the transmitting coil with respect to a plane passing through the median portion and three lateral branches.

24. A device comprising a central support for carrying a plurality of microdevices for logging a medium in a borehole, each of said microdevices including a transmitting coil and two receiving coils, a second transmitting coil, an electrically insulating, soft magnetic-material circuit serving as a support for each of the coils and which is adjacent the medium and which has a median portion and four lateral, parallel branches perpendicular to the median portion, each of said microdevices also including means for forming a shield between at least one transmitting coil and an area without interest in the medium.

25. A device according to claim 24, wherein each of said microdevices also includes a first supplementary branch on which no coil is wound, said first supplementary branch being adjacent one of the branches carrying a transmitting coil.

26. A device according to claim 25, wherein each of said microdevices also includes a second supplementary branch on which no coil is wound and being adjacent the other branch carrying transmitting coil.

27. A device according to claim 24, wherein each of said microdevices also includes two supplementary branches located on either side of one of the branches carrying a transmitting coil, with respect to a plane passing through the median portion and lateral branches carrying coils.

28. A device according to claim 24, wherein the two transmitting coils of each of said microdevices are located on the two central, lateral branches, and the two outside lateral branches each carry a receiving coil.

29. A device according to claim 28, wherein each of said microdevices also includes two supplemental branches located on either side of at least one of the branches carrying a transmitting coil, with respect to a plane passing through the median portion and the lateral branches carrying coils.

30. A device according to claim 21, wherein each of said microdevices also includes two supplementary branches located on either side of the branch on which is wound the transmitting coil with respect to a plane passing through the median portion and three lateral branches.

31. A device according to claim 22, wherein each of said microdevices also includes two supplementary branches located on either side of the branch on which is wound the transmitting coil with respect to a plane passing through the median portion and three lateral branches.

32. A device according to claim 24, wherein the two receiving coils of each of said microdevices are located on two lateral, central branches, and two outside lateral branches each carrying a transmitting coil.

33. A device according to claim 32, wherein each of the microdevices also includes a fifth lateral branch parallel to the two lateral central branches and the two outside lateral branches as well as a third receiving coil, the coils being connected in the following order starting from the outermost outside lateral branch: a first transmitting coil, a first receiving coil, a second receiving coil connected in opposition to the first receiving coil, a third receiving coil connected in opposition to the second receiving coil and a second transmitting coil.

* * * * *

UNITED STATES PATENT AND TRADEMARK OFFICE
CERTIFICATE OF CORRECTION

PATENT NO. : 5,606,260
DATED : February 25, 1997
INVENTOR(S) : Patrice Giordano, Henri Glenat, Jean-Michel Ittel and Marcel Locatelli It is certified that error appears in the above-indentified patent and that said Letters Patent is hereby corrected as shown below:

Claim 10, Column 8, Line 16, "an," should be --and--.

Claim 26, Column 10, Line 2, insert --a-- after "carrying".

Signed and Sealed this

Thirteenth Day of May, 1997

*Attest:*

BRUCE LEHMAN

*Attesting Officer*   Commissioner of Patents and Trademarks